United States Patent [19]

Tronzo et al.

[11] Patent Number: 5,658,339
[45] Date of Patent: Aug. 19, 1997

[54] COMPRESSION HIP SCREW PLATE

[75] Inventors: Raymond G. Tronzo, Palm Beach, Fla.; Ben R. Shappley, Germantown, Tex.; Joseph M. Ferrante, Bartlett, Tenn.

[73] Assignee: Wright Medical Technology, Inc., Arlington, Tenn.

[21] Appl. No.: 583,430

[22] Filed: Jan. 5, 1996

[51] Int. Cl.⁶ ............................................. A61F 2/32
[52] U.S. Cl. ............................. 623/18; 623/22; 623/23; 606/65; 606/66; 606/67; 606/68
[58] Field of Search ......................... 606/65, 66, 67, 606/68; 623/18, 22, 23

[56] References Cited

U.S. PATENT DOCUMENTS

| | | | |
|---|---|---|---|
| 2,496,126 | 1/1950 | Haboush | 606/67 |
| 2,834,342 | 5/1958 | Yost | 606/67 |
| 4,095,591 | 6/1978 | Graham, Jr. et al. | 606/66 |
| 4,612,920 | 9/1986 | Lower | 5/4 |
| 4,988,350 | 1/1991 | Herzberg | 606/65 |
| 5,462,547 | 10/1995 | Weigum | 606/65 |
| 5,484,439 | 1/1996 | Olson et al. | 606/65 |

*Primary Examiner*—John G. Weiss
*Assistant Examiner*—Francis K. Cuddihy
*Attorney, Agent, or Firm*—Walker, McKenzie & Walker, P.C.

[57] ABSTRACT

A compression hip screw plate for a hip screw system used to compress a proximal femur having a shaft with a lateral aspect and a neck extending from the shaft at an anteverted angle, both of which follow the anatomical contours of the proximal femur. The compression hip screw plate may include a side plate having a face side attachable to the lateral aspect of the shaft of the proximal femur; and a barrel having a first end extendable through the lateral aspect of the shaft of the proximal femur and into the neck of the proximal femur, and having a second end attached to the side plate with the first end extending away from the face side of the barrel at an anteverted angle. The compression hip screw plate may include a side plate with an anterior bow to match the natural femur.

6 Claims, 4 Drawing Sheets

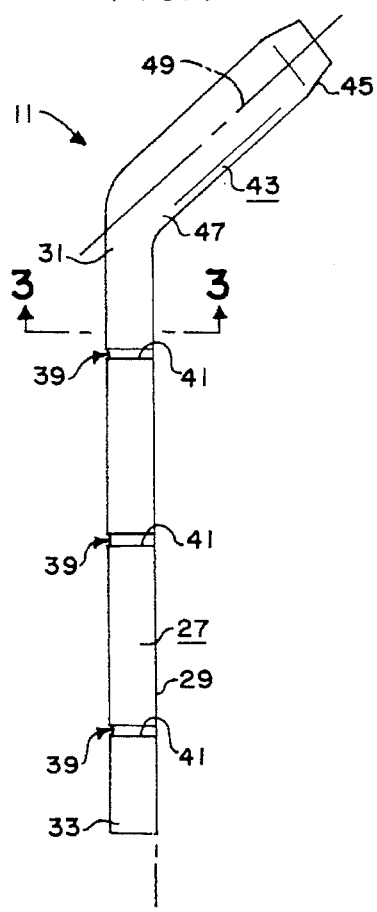
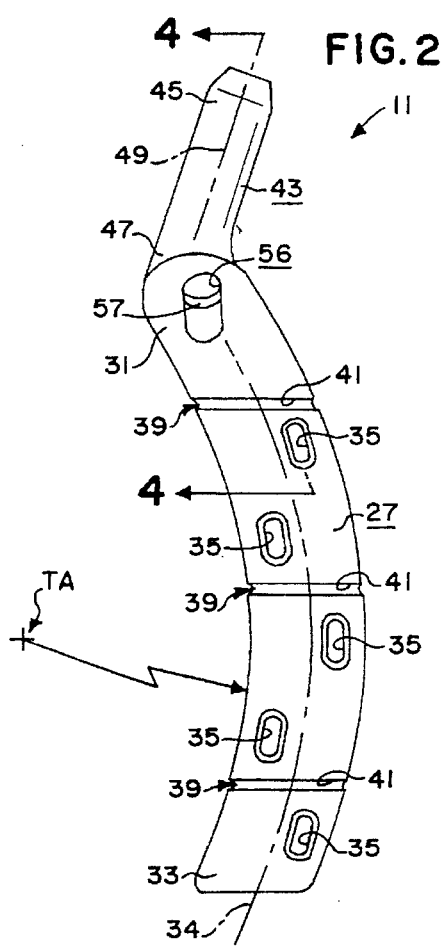
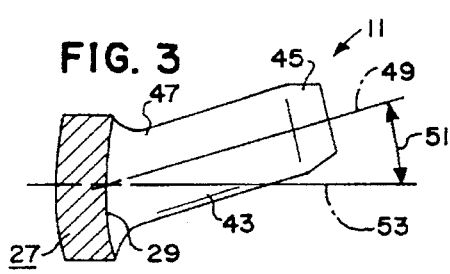
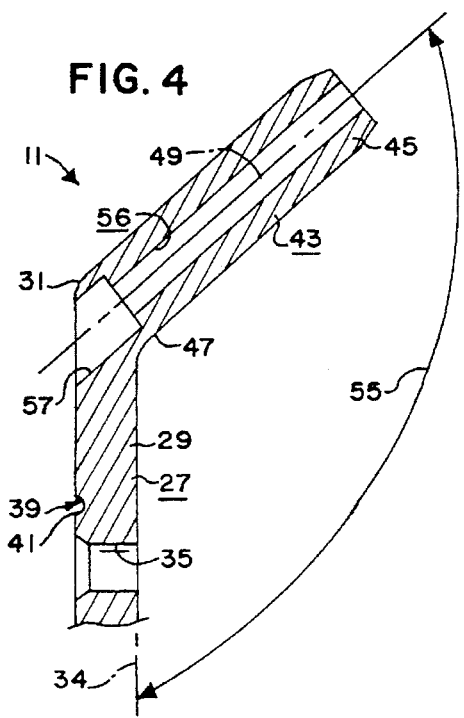
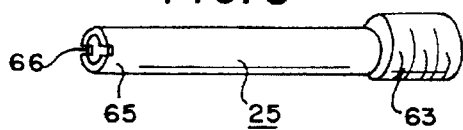
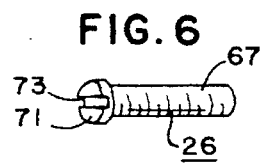

FIG. 15
FIG. 16
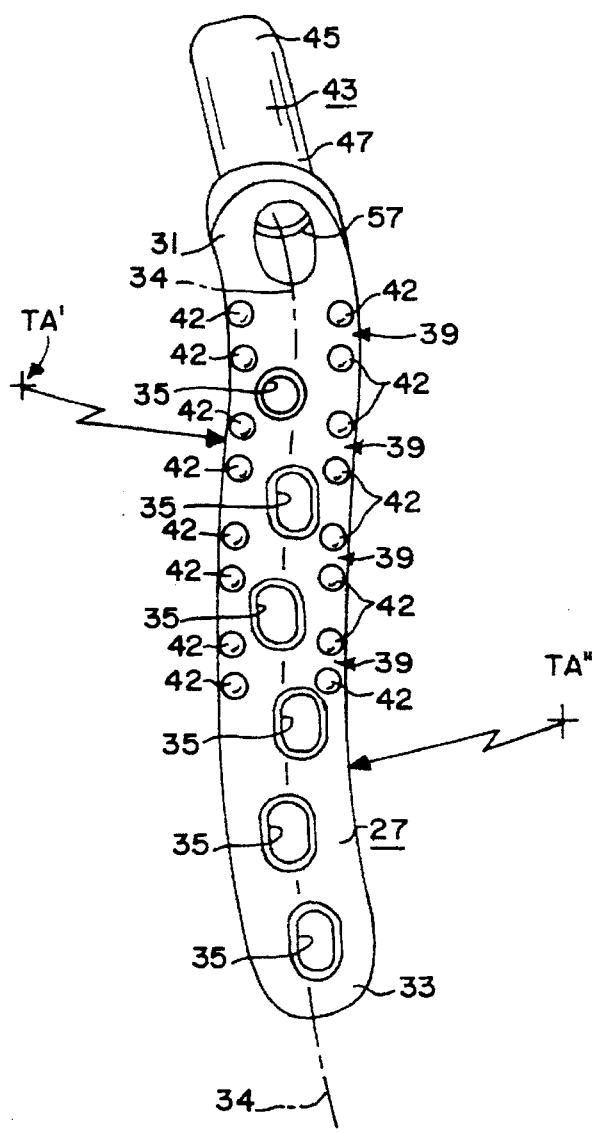
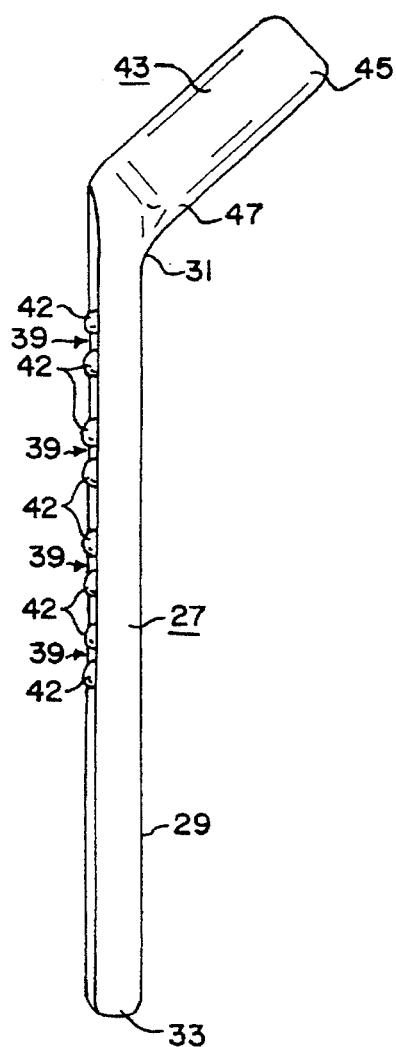

COMPRESSION HIP SCREW PLATE

BACKGROUND OF THE INVENTION

1. Field of the Invention

The present invention relates in general to hip screw systems for fixing proximal femurs and more specifically to an improved compression hip screw plate having an anteverted barrel and/or a bowed side plate.

2. Information Disclosure Statement

Hip screw systems typically include a lag screw for extending through a femoral neck and for being fixed to a femoral head, a compression hip screw plate having a barrel for receiving the outer end of the lag screw and having a side plate for being fixed to the lateral aspect of a femoral shaft, and a compression screw for joining the lag screw and screw plate together in such a manner to cause the femoral head, neck and shaft to be held in compression, etc. Such hip screw systems are commonly used to secure trochanteric, neck and head fractures of the upper or proximal end of femurs, and may a/so be modified to fix fractures of the supracondylar area of the femur.

Lower, U.S. Pat. No. 4,612,920, issued Sep. 23, 1986, discloses a basic compression hip screw system including a lag screw for extending through the upper shaft and neck and into the head of a femur; a screw plate having a barrel for extending into the upper shaft of the femur and over the outer end of the lag screw and having a side plate for being fixed to the lateral aspect of the femur; a compression screw for joining the lag screw to screw plate in a manner to place the upper shaft, neck and head of the femur in compression; and a locking pin for fitting in coacting grooves in the lag screw and barrel to selectively prevent rotation of the lag screw with respect to the barrel.

Prior hip screw systems frequently take away the natural anteversion of the femoral neck.

Nothing in the known prior art discloses or suggests the present invention. More specifically, nothing in the known prior art discloses or suggests a compression hip screw plate for a hip screw system with a barrel that is anteverted to match the longitudinal axis of a femoral neck of a proximal femur that is anteverted relative to the lateral axis of the shaft of the proximal femur and/or with a side plate that is bowed to match the bow of the lateral axis of the shaft of the proximal femur.

SUMMARY OF THE INVENTION

The present invention provides an improved compression hip screw plate that allows the plate to be placed anatomically, thereby allowing for easier and more secure placement, resulting in a more correct walking gate after implantation. More simply stated, the present invention aids greatly in restoring normal anatomy to the fractured upper end of the femur where the plate also follows the normal anatomy of the upper femoral shaft. A basic concept of the present invention is to provide a compression hip screw plate for a hip screw system having a barrel that is anteverted to match or coincide with the natural anteverted angle of a femoral neck to the lateral axis or aspect of the shaft of a proximal femur. Another concept of the present invention is to provide a compression hip screw plate for a hip screw system with a side plate having an anatomic bow to match the natural bow of the lateral axis or aspect of the shaft of a proximal femur.

The compression hip screw plate of the present invention includes a side plate and a barrel extending from the side plate at a primary angle. The improvements of the present invention includes extending the barrel from the side plate at an anteverted angle and/or bowing the side plate anteriorly.

The present invention will also facilitate the surgical application and reduction of the fracture fragments of the fracture site in question.

The material for the implant of the present invention may be any current, past, present, and future material suitable to the function of this device.

BRIEF DESCRIPTION OF THE DRAWINGS

FIG. 1 is an anterior elevational view of an improved right compression hip screw plate of the present invention.

FIG. 2 is a lateral elevational view of the compression screw plate of FIG. 1.

FIG. 3 is somewhat enlarged sectional view substantially as taken on line 3—3 of FIG. 1.

FIG. 4 is a somewhat enlarged sectional view substantially as taken on line 4—4 of FIG. 2.

FIG. 5 is a perspective view of a typical lag screw of a hip screw system for use with the improved compression hip screw plate of the present invention.

FIG. 6 is a perspective view of a typical compression screw of a hip screw system for use with the improved compression hip screw plate of the present invention.

FIG. 15 is a lateral elevational view of an improved left compression hip screw plate of the present invention, showing a somewhat modified version.

FIG. 16 is an anterior elevational view of the compression hip screw plate of FIG. 15.

DESCRIPTION OF THE PREFERRED EMBODIMENT

Figure 7:
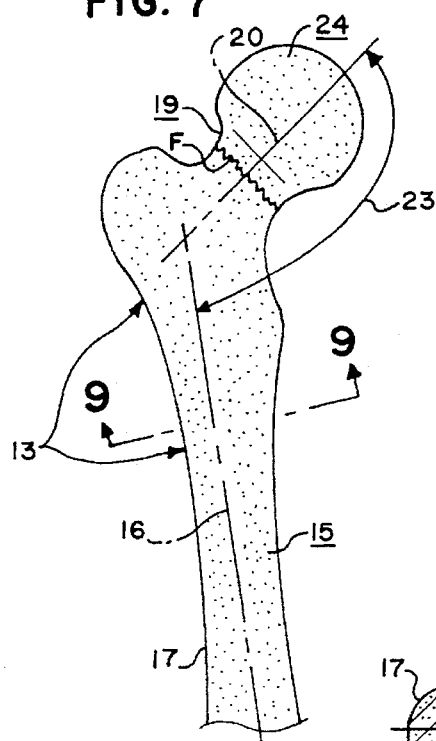
FIG. 7 is an anterior elevation of a right proximal femur with a fractured neck.
Figure 8:
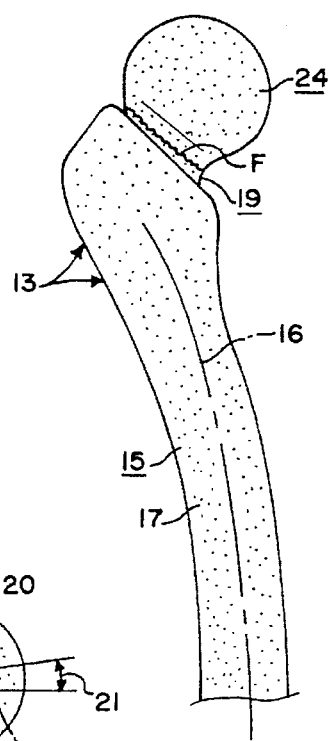
FIG. 8 is a lateral elevation of a fight proximal femur with a fractured neck.
Figure 9:
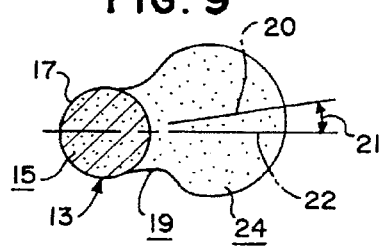
FIG. 9 is a sectional view substantially as taken on line 9—9 of FIG. 7.
Figure 10:
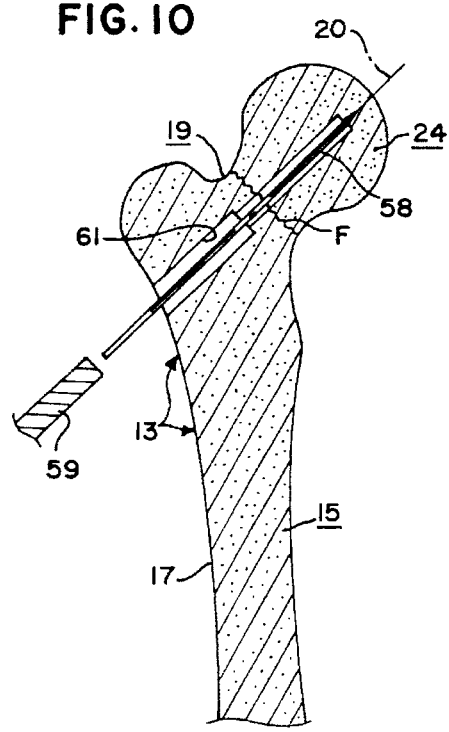
FIG. 10 is a somewhat diagrammatic sectional view of the proximal femur of FIG. 7 but showing a guide pin inserted from the proximal shaft, through the neck and into the head thereof; and showing a drill associated with the guide pin and a bore formed by the drill about the guide pin.
Figure 11:
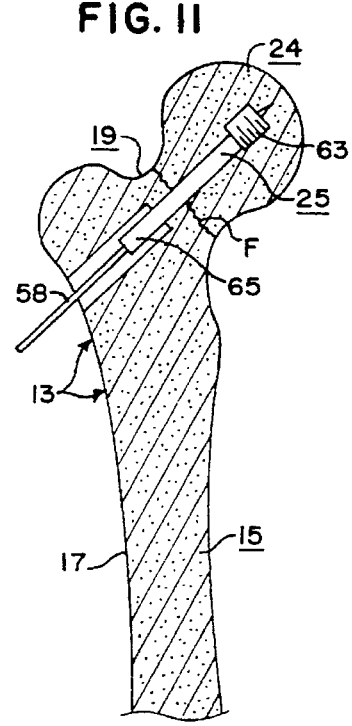
FIG. 11 is a similar to FIG. 10 but shows a lag screw extending through the bore, along the guide pin, between the fractured portions of the proximal femur.
Figure 12:
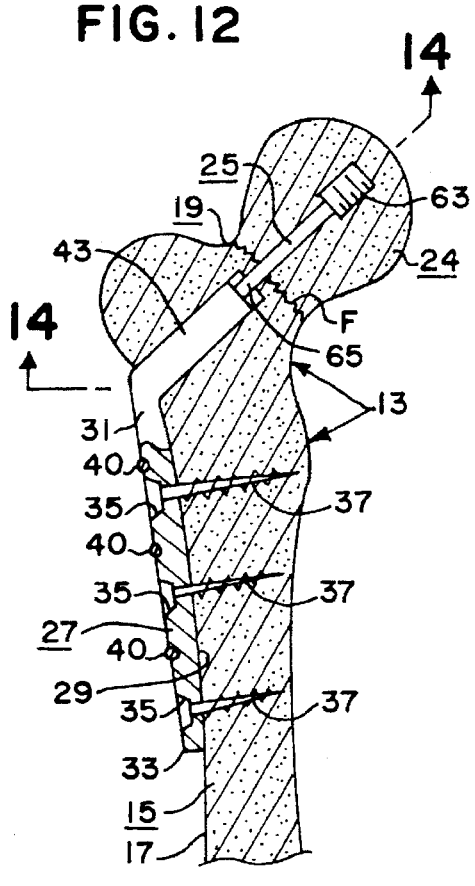
FIG. 12 is similar to FIG. 11 but shows the compression hip screw plate of the present invention attached to the shaft of the proximal femur with bone screws.
Figure 13:
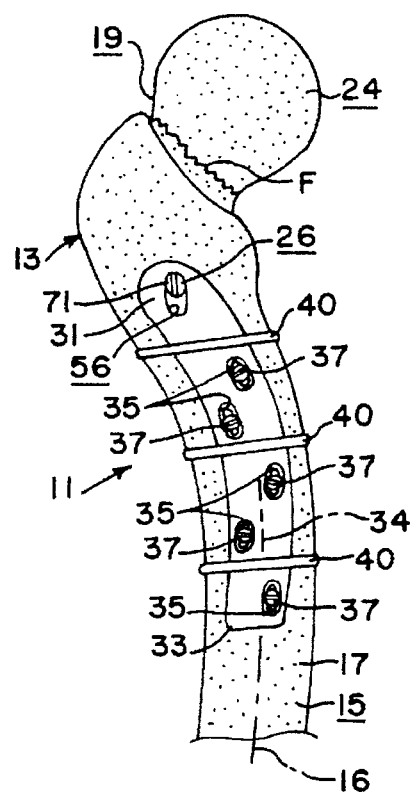
FIG. 13 is a somewhat diagrammatic lateral elevation of FIG. 12 but showing the compression hip screw plate of the present invention attached to the shaft of the proximal femur with optional cables.

The preferred embodiment of the improved compression hip screw plate of the present invention is shown in FIGS. 1–4 and 12–14, and identified by the numeral 11. The screw plate 11 is for a hip screw system used to fix and compress a fracture F, etc., of a proximal femur 13 (see FIGS. 7–14) having a shaft 15 with a lateral axis 16 and a lateral aspect or side 17, having a neck 19 extending from the shaft 15 with the longitudinal axis 20 extending from the shaft 15 at an anteverted angle 21 with respect to a coronal plane 22 extending through the lateral axis 16 of the shaft 15 (see, in general, FIG. 9) and at a primary angle 23 with respect to the lateral axis 16 of the shaft 15 (see, in general, FIG. 7), and having a head 24 extending from the neck 19. The head 24 articulates with the acetabulum of the pelvis (not shown). The lateral axis 16 of the shaft 15 is bowed anteriorly when view from the lateral aspect 17 as clearly shown in FIG. 8.

The hip screw system also includes a lag screw 25 (see FIGS. 5, 11, 12 and 14) for extending through the neck 19 and being fixed to the head 24, and a compression screw 26 (see FIGS. 6 and 14) for joining the lag screw 25 and screw plate 11 together in such a manner to cause the head 24, neck 19 and shaft 15 to be held in compression, etc.

Figure 14:
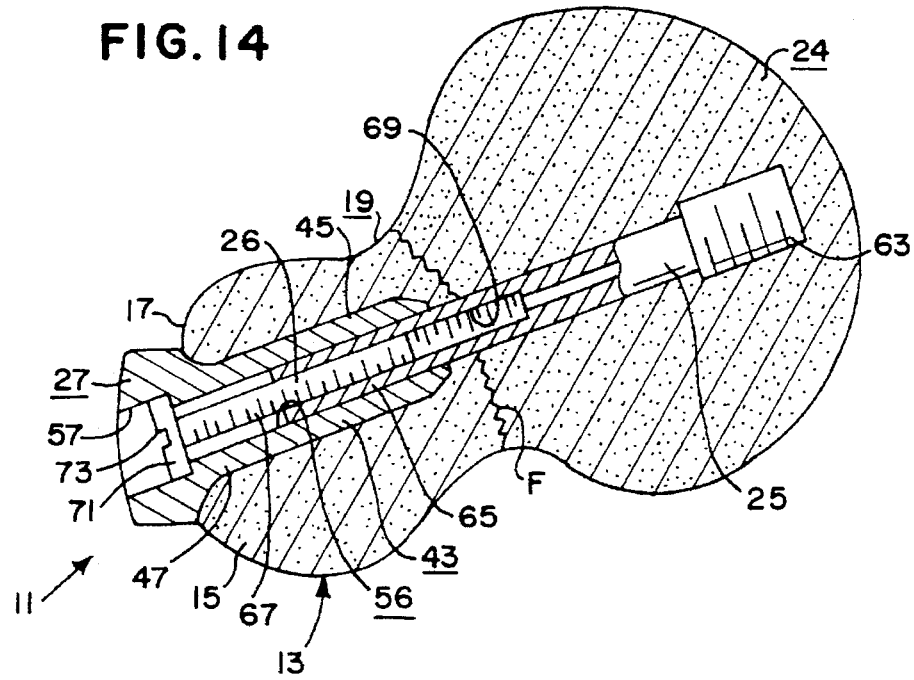
FIG. 14 is a somewhat enlarged sectional view substantially as taken on line 14—14 of FIG. 12.

The screw plate 11 includes a side plate 27 having a face side 29 attachable to the lateral aspect 17 of the shaft 15 of the proximal femur 13. The side plate 27 is preferably elongated, having a generally superior first end 31 and a generally inferior second end 33 with a lateral longitudinal axis 34 extending between the first and second ends 31, 33 (see, in general, FIG. 2). The side plate 27 is preferably bowed along the longitudinal axis 34 anteriorly from the first end 31 about a generally transverse axis as clearly shown in FIGS. 2 and 13 to match the bowed lateral axis 16 of the shaft 15 of the proximal femur 13. The amount of bow may vary depending on patient anatomy, etc. The side plate 27 shown in FIGS. 2 and 13 has a relatively sharp, single bow along the longitudinal axis 34 anteriorly from the first end 31 about a single generally transverse axis TA. Alternatively, the side plate 27 shown in FIG. 15 has a pair of relatively mild bows along the longitudinal axis 34 extending first posteriorly from the first end 31 about a first transverse axis TA', and then extending anteriorly about a second transverse axis TA" thus forming a generally S-shaped curve for the fight femur and a generally reverse S-shaped curve for the left femur (a left compression hip screw plate for a left femur is shown in FIG. 14) as will now be apparent to those skilled in the art. The face side 29 of the side plate 27 may be curved about a longitudinal axis to match the curved lateral aspect 17 of the shaft 15 of the proximal femur 13. The side plate 27 preferably has a plurality of spaced apertures 35 therethrough for allowing typical bone screws 37 or the like to be used to secure the side plate 27 to the lateral aspect 17 of the shaft 15 of the proximal femur 13 (see, in general, FIGS. 12 and 13) as will now be apparent to those skilled in the art. In addition, the side plate 27 may have a plurality of spaced transverse guideways 39, etc., across the outer side thereof for optionally allowing cerclage wire or cable 40, etc., to be used to tie or secure the side plate 27 to the lateral aspect 17 of the shaft 15 of the proximal femur 13 (see FIG. 13) as will now be apparent to those skilled in the art. The guideways 39 may be formed by slots or grooves 41 made into the outer side and edges of the side plate 27 as shown in FIGS. 1, 2, 4 and 12. Alternatively, the guideways 39 may be formed by a plurality of spaced bumps or protrusions 42 on the outer side of the side plate 27 as shown in FIGS. 15 and 16.

The screw plate 11 includes a barrel 43 having a first end 45 for extending through the lateral aspect 17 of the shaft 15 of the proximal femur 13 and into the neck 19 of the proximal femur 13, having a second end 47 attached to the first end 31 of the side plate 27, and having a longitudinal axis 49 extending between the first and second ends 45, 47 thereof. The barrel 43 preferably extends from the side plate 27 with the longitudinal axis 49 at an anteverted angle 51 with respect to a coronal plane 53 extending through the longitudinal axis 34 of the side plate 27 (see, in general, FIG. 3) and at a primary angle 55 with respect to the longitudinal axis 34 of the side plate 27 (see, in general, FIG. 4). The anteverted angle 51 is preferably substantially equal to the anteverted angle 21 of the proximal femur 13 and may vary from 1° or less to 25° or more. Preferably, the anteverted angle 21 is 11.5°. The primary angle 55 is preferably substantially equal to the primary angle 23 of the proximal femur 13 and may vary from 100° or less to over 160°. Preferably, the screw plate 11 is made with primary angles 55 of 135°, 140° and 145°, etc., as will now be apparent to those skilled in the art. The barrel 43 preferably has a passageway 56 extending completely therethrough for receiving a portion of the lag screw 25 and the compression screw 26. The passageway 56 preferably has an enlarged outer end forming a seat 57 for reasons which will hereinafter become apparent.

The side plate 27 and barrel 43 are preferably machined or otherwise manufactured as an integral, one-piece unit out of a surgical grade metal such as, for example, stainless steel, or other metallurgical substances, or out of bioresorbable or biodegradable materials, in various sizes and lengths, etc., as will now be apparent to those skilled in the art. It should be noted that the screw plate 11 shown in FIGS. 1–4 and 12–13 is designed for a right proximal femur and that a screw plate 11 designed for a left proximal femur will be a mirror image thereof as will now be apparent to those skilled in the art.

The surgical procedure for fixing and compressing a fracture F in or adjacent the neck 19 of a proximal femur 13, etc., using the present invention can vary as will now be apparent to those skilled in the art. Preferably, the proximal femur 13 is exposed in any typical manner and a guide pin 58 such as a well-known Kirschner or "K" wire is inserted or "drilled" through the lateral aspect 17 of the shaft 15 of the proximal femur 13, through the neck 19 of the proximal femur 13, and into the head 24 of the proximal femur 13 along the longitudinal axis 20 of the neck 19 as clearly shown in FIG. 10. A drill or reamer 59 is then used to form a guide bore 61 for the lag screw 25 and barrel 43. The drill or reamer 59 may be cannulated for use with a guide pin 58 to insure proper positioning of the bore 61 along the longitudinal axis 20, etc. Next, the lag screw 25 is screwed into the bore 61 with the threaded head 63 of the lag screw 25 secured to the head 24 of the proximal femur 13. The lag screw 25 may be cannulated for using with a guide pin 58 to insure proper positioning thereof along the longitudinal axis 20, etc. The outer end 65 of the lag screw 25 preferably includes means such as a slot 66, non-round cavity or projection, etc., to allow the lag screw 25 to be screwed into the head 24 with a tool such as a screwdriver or the like as will now be apparent to those skilled in the art. Next, the barrel 43 of the screw plate 11 (FIGS. 1 and 2) is slipped into the bore 61 until the outer end 65 of the lag screw 25 extends into the mouth of the passageway 56 in the barrel 43. The side plate 27 is then secured to the lateral aspect 17 of the shaft 15 of the proximal femur 13 using the bone screws 37 and/or cables 40 with the longitudinal axis 34 thereof substantially aligned with the lateral axis 16 of the shaft 15 and with the longitudinal axis 49 of the barrel 43 substantially aligned with the longitudinal axis 20 of the neck 19 of the proximal femur 13. The threaded end 67 of the compression screw 26 is then inserted into the passageway 56 until it engages a threaded aperture 69 in the outer end 65 of the lag screw 25. The optional compression screw 26 can then be screwed into the threaded aperture 69 until the head 71 of the compression screw 26 engages the seat 57 in the passageway 56 through the barrel 43, causing the fracture F to be fixed and compressed as will now be apparent to those skilled in the art. The head 71 of the compression screw 26 preferably includes means such as a slot 73, non-round cavity or projection, etc., to allow the compression screw 26 to be screwed into the threaded aperture 69 with a tool such as a screwdriver or the like as will now be apparent to those skilled in the art.

As thus constructed and used, the present invention provides an improved compression hip screw plate that can be placed anatomically, unlike current plates that must be place off the anatomic axis; that allows for easier placement and for a correct walking gate instead of a toe-in stance which is currently seen with current designs.

Although the present invention has been described and illustrated with respect to a preferred embodiment and a preferred use therefor, it is not to be so limited since modifications and changes can be made therein which are within the full intended scope of the invention. For example, the present invention could be used for solid nails rather than sliding nails or sliding screws.

We claim:

1. A compression hip screw plate comprising:
   (a) a side plate having a first end, a second end remote from said first end of said side plate, a longitudinal axis extending between said first and second ends of said side plate, and a face surface; and
   (b) a barrel having a first end, a second end remote from said first end of said barrel, and a longitudinal axis extending between said first and second ends of said barrel; said barrel being attached to said side plate with said longitudinal axis of said barrel anteverted with respect to a coronal plane extending substantially perpendicular to said face surface of said side plate at the intersection of said longitudinal axis of said barrel and said face surface of said side plate, and with said longitudinal axis of said barrel non-parallel with respect to a sagittal plane extending substantially parallel to said face surface of said side plate at the intersection of said longitudinal axis of said barrel and said face surface of said side plate.

2. The compression hip screw plate of claim 1 in which said longitudinal axis of said side plate is bowed about an axis extending substantially perpendicular to the sagittal plane extending substantially parallel to said face surface of said side plate at the intersection of said longitudinal axis of said barrel and said face surface of said side plate.

3. The compression hip screw plate of claim 1 in which said longitudinal axis of said side plate is bowed anteriorly from said first end thereof to said second end thereof about an axis extending substantially perpendicular to the sagittal plane extending substantially parallel to said face surface of said side plate at the intersection of said longitudinal axis of said barrel and said face surface of said side plate.

4. The compression hip screw plate of claim 1 in which said longitudinal axis of said side plate is bowed first posteriorly from said first end of said side plate and then anteriorly to said second end of said side plate about axes extending substantially perpendicular to the sagittal plane extending substantially parallel to said face surface of said side plate at the intersection of said longitudinal axis of said barrel and said face surface of said side plate.

5. A compression hip screw plate comprising:
   (a) a side plate having a first end, a second end remote from said first end of said side plate, a longitudinal axis extending between said first and second ends of said barrel, and a face surface; said longitudinal axis of said side plate being bowed about an axis extending substantially perpendicular to a sagittal plane extending substantially parallel to said face surface of said side plate; and
   (b) a barrel having a first end, a second end remote from said first end, and a longitudinal axis extending between said first and second ends; said second end of said barrel being attached to said first end of said side plate.

6. An improved hip screw system for fixing a proximal femur having an anteriorly bowed shaft with a lateral aspect and a neck extending from said shaft at an anteverted angle; wherein said improvement comprises a compression hip screw plate including:
   (a) an elongated side plate having a face side attachable to said lateral aspect of said shaft of said proximal femur, a first end, a second end remote from said first end of said side plate, and a longitudinal axis extending between said first and second ends of said side plate with said longitudinal axis of said side plate bowed anteriorly about an axis extending substantially perpendicular to a sagittal plane extending substantially parallel to said face surface of said side plate; and
   (b) a barrel having a first end extendable through said lateral aspect of said shaft of said proximal femur and into said neck of said proximal femur, having a second end attached to said side plate, and having a longitudinal axis extending between said first and second ends of said barrel with said barrel attached to said face side of said side plate, with said longitudinal axis of said barrel anteverted with respect to a coronal plane extending substantially perpendicular to said face surface of said side plate at the intersection of said longitudinal axis of said barrel and said face surface of said side plate, and with said longitudinal axis of said barrel non-parallel with respect to the sagittal plane extending substantially parallel to said face surface of said side plate at the intersection of said longitudinal axis of said barrel and said face surface of said side plate.

* * * * *

UNITED STATES PATENT AND TRADEMARK OFFICE
CERTIFICATE OF CORRECTION

PATENT NO. : 5,658,339
DATED : August 19, 1997
INVENTOR(S) : Raymond G. Tronzo, et. al.

It is certified that error appears in the above-identified patent and that said Letters Patent is hereby corrected as shown below:

Title page, item [75], inventor: Ben R. Shappley, Germantown, Tenn.--.

Signed and Sealed this

Thirteenth Day of January, 1998

Attest:

BRUCE LEHMAN

Attesting Officer

Commissioner of Patents and Trademarks